United States Patent
Rains et al.

(10) Patent No.: US 8,050,814 B2
(45) Date of Patent: Nov. 1, 2011

(54) APPARATUS AND METHOD FOR DETERMINING REMAINING TRANSMISSION OIL LIFE

(75) Inventors: Mark A. Rains, Indianapolis, IN (US); Brett R. Caldwell, New Palestine, IN (US)

(73) Assignee: GM Global Technology Operations LLC, Detroit, MI (US)

( * ) Notice: Subject to any disclaimer, the term of this patent is extended or adjusted under 35 U.S.C. 154(b) by 952 days.

(21) Appl. No.: 12/018,833

(22) Filed: Jan. 24, 2008

(65) Prior Publication Data

US 2008/0228339 A1 Sep. 18, 2008

Related U.S. Application Data

(60) Provisional application No. 60/895,017, filed on Mar. 15, 2007.

(51) Int. Cl.
*G01N 33/26* (2006.01)

(52) U.S. Cl. ......... 701/30; 340/457.4; 73/53.05; 701/51

(58) Field of Classification Search ............ 701/29, 701/30, 51; 340/438, 439, 457.4; 73/53.05, 73/54.01
See application file for complete search history.

(56) References Cited

U.S. PATENT DOCUMENTS

| | | | | |
|---|---|---|---|---|
| 4,497,200 A * | 2/1985 | Tournier | ...................... | 73/53.05 |
| 4,506,337 A * | 3/1985 | Yasuhara | ........................ | 701/30 |
| 4,629,334 A | 12/1986 | Hochstein | | |
| 4,677,847 A * | 7/1987 | Sawatari et al. | ............. | 73/53.05 |
| 4,706,193 A * | 11/1987 | Imajo et al. | ..................... | 701/30 |
| 4,742,476 A * | 5/1988 | Schwartz et al. | ............... | 701/30 |
| 4,796,204 A * | 1/1989 | Inoue | ......................... | 123/196 S |
| 4,839,831 A * | 6/1989 | Imajo et al. | .................. | 73/53.05 |
| 4,845,623 A * | 7/1989 | Korb | ............................. | 701/101 |
| 4,847,768 A * | 7/1989 | Schwartz et al. | ............... | 701/30 |
| 5,043,697 A * | 8/1991 | Ayabe et al. | ............... | 340/457.4 |
| 5,060,156 A * | 10/1991 | Vajgart et al. | .................. | 701/30 |
| 5,382,942 A * | 1/1995 | Raffa et al. | ................ | 340/457.4 |
| 5,530,647 A * | 6/1996 | Sem et al. | ........................ | 701/30 |
| 5,559,494 A | 9/1996 | Thompson | | |
| 5,750,887 A * | 5/1998 | Schricker | .................. | 73/114.55 |
| 5,777,211 A * | 7/1998 | Binienda et al. | ............. | 73/53.05 |
| 5,969,601 A * | 10/1999 | Sato et al. | .................. | 340/450.3 |
| 6,037,864 A * | 3/2000 | Sem et al. | .................. | 340/457.4 |
| 6,208,245 B1 * | 3/2001 | Post et al. | .................. | 340/457.4 |
| 6,253,601 B1 * | 7/2001 | Wang et al. | ................ | 73/114.55 |
| 6,266,587 B1 * | 7/2001 | Guertler et al. | ................. | 701/30 |
| 6,327,900 B1 * | 12/2001 | Mc Donald et al. | ........ | 73/114.55 |
| 6,449,538 B1 * | 9/2002 | Kubo et al. | ..................... | 701/30 |
| 6,513,368 B2 * | 2/2003 | Bondarowicz et al. | ...... | 73/53.05 |

(Continued)

*Primary Examiner* — Darnell Jayne
*Assistant Examiner* — Joshua Rodden
(74) *Attorney, Agent, or Firm* — Quinn Law Group, PLLC

(57) ABSTRACT

An improved method for predicting the remaining useful life of transmission oil and an apparatus for practicing the same are provided. The method includes: detecting if the transmission has completed a new shift; if yes, determining a total shift count; determining accumulated distance and accumulated time parameters; determining a transmission temperature degradation factor; detecting if the lockup clutch is open and if the transmission is in range; if yes, determining a converter degradation factor; determining a total degradation factor based at least in part upon the transmission temperature degradation factor and converter degradation factor; determining an oil life time limit and oil life distance limit; determining if either the accumulated time parameter is greater than the oil life time limit or the accumulated distance parameter is greater than the oil life distance limit; if yes, activating a service indicator to notify vehicle occupants that transmission oil service is required.

19 Claims, 3 Drawing Sheets

U.S. PATENT DOCUMENTS

| | | | |
|---|---|---|---|
| 6,580,366 B1 * | 6/2003 | Engfehr | 340/457.4 |
| 6,741,938 B2 * | 5/2004 | Berndorfer | 702/23 |
| 6,817,455 B1 * | 11/2004 | Gazyakan et al. | 188/290 |
| 6,859,039 B2 * | 2/2005 | Horie et al. | 324/438 |
| 6,901,788 B2 * | 6/2005 | Han et al. | 73/53.05 |
| 6,917,865 B2 * | 7/2005 | Arai et al. | 701/30 |
| 6,920,412 B1 * | 7/2005 | Sarkar et al. | 702/181 |
| 6,920,779 B2 * | 7/2005 | Carlstrom et al. | 73/53.05 |
| 7,433,770 B2 * | 10/2008 | Inagawa et al. | 701/51 |
| 7,826,987 B2 * | 11/2010 | Aikawa | 702/50 |
| 7,852,201 B2 * | 12/2010 | Rains et al. | 340/438 |
| 2002/0112529 A1 * | 8/2002 | Bondarowicz et al. | 73/53.05 |
| 2004/0093150 A1 * | 5/2004 | Arai et al. | 701/104 |
| 2004/0117147 A1 * | 6/2004 | Hirthe et al. | 702/181 |
| 2005/0131599 A1 * | 6/2005 | Inagawa et al. | 701/29 |
| 2008/0228339 A1 * | 9/2008 | Rains et al. | 701/29 |

\* cited by examiner

APPARATUS AND METHOD FOR DETERMINING REMAINING TRANSMISSION OIL LIFE

CLAIM OF PRIORITY AND CROSS-REFERENCE TO RELATED APPLICATIONS

This application claims the benefit of and priority to U.S. Provisional Patent Application No. 60/895,017, filed on Mar. 15, 2007, which is hereby incorporated by reference in its entirety.

TECHNICAL FIELD

The present invention pertains generally to methods for predicting the remaining useful life of transmission oil and devices for practicing the same.

BACKGROUND OF THE INVENTION

Almost all modern day automobiles include a powertrain that is comprised of an engine and/or motor in power flow communication with a final drive system via a multi-speed power transmission. To operate properly, the traditional power transmission requires a continuous supply of pressurized fluid, such as conventional transmission oil. The pressurized fluid may be used for such functions as cooling, lubrication, and torque converter operation. It is well known that the lubricating and cooling capabilities of transmission oil systems greatly impact the reliability and durability of the transmission. Additionally, multi-speed power transmissions require pressurized fluid for controlled engagement and disengagement, on a desired schedule, of the various torque transmitting mechanisms that operate to establish the speed ratios within the internal gear arrangement.

The transmission's lubricating and cooling capabilities tend to degrade with transmission operation and over time. Contamination of the oil by water, particulate matter, such as dust or carbon, and oil degradation by-products affect the ability of the transmission oil to lubricate, cool, and protect critical transmission parts. Accordingly, most original equipment manufacturers (OEMs) provide guidelines for determining when the transmission oil should be changed. Such guidelines are typically stated with respect to a measurable period of operation or a period of time.

Though most transmissions have associated guidelines for the frequency of oil changes or service, more frequent changes may be required if the transmission is subjected to extreme operating conditions which may effect high levels of contamination or overheating. For instance, it has been found that excessive degradation of the transmission oil occurs at high temperatures. At elevated transmission oil temperatures, antioxidants in the oil become depleted and the oil becomes more viscous and acidic due to increased oxidation. Depending upon the transmission operating conditions, the oil change interval may be less than 50 percent of traditional guidelines, or may exceed the guidelines by 200 percent or more.

SUMMARY OF THE INVENTION

The present invention provides an improved method for determining the remaining useful life of transmission oil in an automatic transmission, and devices for practicing the same. The methods in accordance with the present invention provide for a more accurate assessment of the remaining useful life of transmission oil by taking into consideration parameters not normally accounted for in the prior art. As such, the present invention allows for advance indications of transmission oil service requirements thereby allotting for realized extended oil life and enhanced transmission performance.

According to one preferred embodiment of the present invention, an improved method or algorithm is provided for predicting the remaining useful life of oil in a vehicle transmission, preferably in the nature of a multi-speed power transmission having a torque converter assembly with a lockup clutch. The method includes the steps of: detecting if the transmission has completed a new shift; determining a total shift count if the new shift has completed; determining an accumulated time parameter and an accumulated distance parameter; monitoring a transmission temperature; determining a transmission temperature degradation factor; determining a total degradation factor based, at least in part, upon the transmission temperature degradation factor; determining an oil life time limit and an oil life distance limit each based, at least in part, upon the total degradation factor; determining if either the accumulated time parameter is greater than the oil life time limit or the accumulated distance parameter is greater than the oil life distance limit; if yes, responding by activating a service indicator configured to notify vehicle occupants that transmission oil service is required. Ideally, determining the transmission temperature degradation factor is based, at least in part, upon a transmission temperature fuzzy timer parameter.

Preferably, the method also includes detecting if the torque converter lockup clutch is open and if the transmission is in range. If the lockup clutch is open and the transmission is in range, the algorithm will calculate or determine a converter degradation factor. Correspondingly, the step of determining the total degradation factor accounts for the converter degradation factor. Ideally, determining the converter degradation factor is based, at least in part, upon a converter fuzzy timer parameter.

It is further preferred that the method also include detecting if the transmission was built with a transmission retarder (i.e., a transmission retarder is present). If so, the method responds by determining a retarder present degradation factor. To this regard, the method subsequently detects if the transmission retarder is active. In response to the transmission retarder being active, the method includes determining a retarder active degradation factor. Correspondingly, the step of determining the total degradation factor further accounts for the retarder present degradation factor and the retarder active degradation factor. Ideally, determining the retarder active degradation factor is based, at least in part, upon a retarder fuzzy miles parameter.

It is even further preferred that the method also includes detecting if a retarder accumulator is applied. If the accumulator is applied, the method subsequently determines a total number of accumulator applies and calculates an accumulator degradation factor. Correspondingly, the step of determining the total degradation factor accounts for the accumulator degradation factor.

It is even further preferred that the method also includes determining at least one of, but preferably both, a remaining useful distance of the transmission oil and a remaining useful time of the transmission oil. It is desired, in this instance, that the service indicator be configured to selectively provide the remaining useful distance and the remaining useful life to the occupants of the vehicle. Optionally, the service indicator is configured to be cleared or disabled by an operator of the vehicle, a service tool, or both.

According to another preferred embodiment of the present invention, a control apparatus is provided which can determine the useful life of transmission oil in a transmission. The controller is intended for, but not limited to, a motorized vehicle with a power transmission having a torque converter with a lockup clutch, and a reservoir fluidly coupled to and configured for supplying transmission oil to the power transmission. The control apparatus includes a controller, also referred to hereinafter as an electronic control unit (ECU), operatively connected to the power transmission. At least one, but preferably a multitude of sensor devices are in communication with or connected to the controller and configured to monitor, track, or detect various transmission degradation factors and transmit signals indicative thereof to the controller. A service indicator connected to or in communication with the controller, and configured to signal that transmission oil service is required.

The controller has memory containing an algorithm, which in turn is programmed and configured to determine the following: a total degradation factor based, at least in part, upon the sensor signals; an accumulated time parameter and an accumulated distance parameter of the transmission oil; and, an oil life time limit and oil life distance limit based, at least in part, upon the total degradation factor. The controller is also programmed and configured to determine if either the accumulated hours variable is greater than the oil life time limit or the accumulated miles variable is greater than the oil life distance limit. If either the accumulated time parameter is greater than the oil life time limit or the accumulated distance parameter is greater than the oil life distance limit, the controller activates the service indicator to notify vehicle occupants that service of the transmission oil is required.

It is preferred that the degradation factors monitored, tracked, or detected by the sensor devices are inclusive of, but not limited to, a transmission temperature degradation factor, a converter degradation factor, a retarder present degradation factor, a retarder active degradation factor, and an accumulator degradation factor. Notably, the list set forth above by which the total degradation factor is determined is non-exhaustive.

Ideally, the controller is also programmed to determine a remaining useful distance of the transmission oil in response to the accumulated miles variable and a remaining useful time of the transmission oil in response to the accumulated time variable. In this instance, it is also preferred that the service indicator device be configured to selectively provide the remaining useful distance and/or the remaining useful time to the occupants of the vehicle. In this regard, the service indicator device is configured to be cleared or disabled by an operator of the vehicle or a service tool.

The above features and advantages, and other features and advantages of the present invention, will be readily apparent from the following detailed description of the preferred embodiments and best modes for carrying out the invention when taken in connection with the accompanying drawings and appended claims.

DESCRIPTION OF THE PREFERRED EMBODIMENTS

Figure 1:
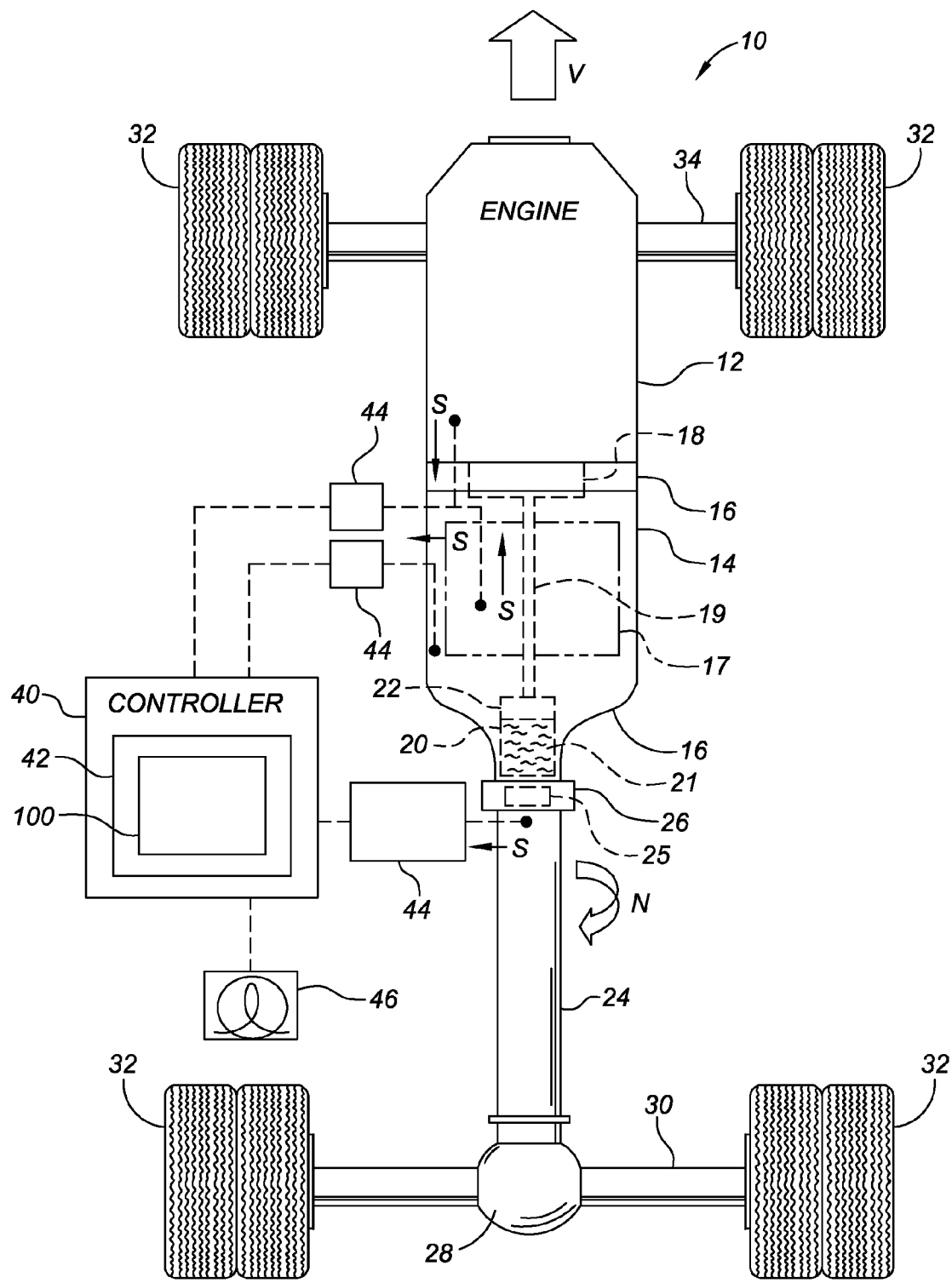
FIG. 1 is a schematic representation of an exemplary vehicle having an oil reservoir fluidly coupled to a transmission, and a plurality of sensors connected to a microprocessor-based control unit for carrying out the control of this invention.

Referring to the drawings, wherein like reference numbers correspond to the same or similar components throughout the several views, there is shown in FIG. 1 a schematic representation of a vehicle 10 having an engine 12 and a transmission 14. The present invention will be described herein with respect to the vehicle 10 as an exemplary application by which the present invention may be incorporated. As such, it should be readily understood that FIG. 1 is merely an exemplary application by which the present invention may be incorporated and practiced—i.e., the present invention is by no means limited to the particular configuration of FIG. 1.

The engine 12 is selectively fluidly connectable to the transmission 14 through a hydrokinetic power coupling device, such as torque converter 16. Alternatively, the engine 12 is selectively mechanically connectable to the transmission 14 through a torque transmitting mechanism, preferably by way of a lockup clutch, shown in phantom in FIG. 1 as 18. In other words, the lockup clutch 18 may be selectively engaged under certain conditions to provide a direct mechanical coupling between the engine 12 and transmission input shaft 19, effectively bypassing the torque converter 16. The transmission 14 includes a plurality of differential gear sets (e.g., planetary gear sets) and clutch packs, collectively depicted in phantom as 17 in FIG. 1, to achieve the necessary transmission of power between the engine 12 and a rotatable output member, such as the driveshaft or transmission output shaft 24.

The transmission 14 also includes or is in fluid communication with a single internal reservoir or sump volume, shown hidden in FIG. 1 at 20, or multiple reservoirs (not shown). The reservoir 20 stores and supplies hydraulic fluid, preferably transmission oil 21, which is pressurized and fed to the transmission 14 by an oil pump assembly 22. Although depicted in FIG. 1 as being packaged inside the transmission housing, the reservoir 20 and pump assembly 22 may be packaged at locations outside of the transmission 14 without departing from the scope and intent of the present invention.

Still referring to FIG. 1, an appropriate retarder 26, having an accumulator (shown with hidden lines as 25 in FIG. 1), may be attached to the output member 24 to serve in vehicle braking and the like. The retarder 26 is preferably a hydrodynamic, i.e. hydraulically-actuated, speed retarding system which is configured to deliver a controllable supply of pressurized fluid, e.g., oil 21, opposite the transmission 14 to thereby induce a viscous drag capable of providing a variable opposing torque suitable for slowing or "retarding" the speed or rate of rotation of the rotatable output member 24 of transmission 14. Alternatively, other transmission speed retarding devices, such as electrodynamic retarders, are also usable in accordance with the present invention.

Output member 24 may be operatively connected to a rear differential 28 configured to distribute rotational force or torque from the output member 24 to a rear drive axle 30 to thereby propel or drive a plurality of wheels 32. Although not shown in FIG. 1, the vehicle 10 may also or alternately include a transfer case and/or front differential suitable for distributing torque to a front drive axle 34 for powering or driving a plurality of wheels 32, such as in a front-wheel drive (FWD), four-wheel drive (4WD), or all-wheel drive (AWD)

configuration. As will be understood by those of ordinary skill in the art, vehicle 10 has an actual vehicle speed, illustrated generally by arrow V that may differ from the transmission output speed, depicted for explanatory purposes by arrow N, depending on, for example, the particular axle ratio of vehicle 10 and the diameter of tires 32.

Vehicle 10 includes a controller, depicted in FIG. 1 in an exemplary embodiment as a micro-processor based electronic control unit (ECU) 40, having a suitable amount of programmable memory 42. The controller 40 is configured or programmed, at least in part, to control the operation of transmission 14. For instance, the controller 40 serves to manage the shifting of the plurality of gear sets and clutch packs 17, operation of torque converter 16 and lockup clutch 18, and the application and release of the retarder 26. The controller 40, namely programmable memory 42, further includes a control method or algorithm 100 for determining or predicting the remaining useful life of the transmission oil 21, as will be discussed in detail below with regard to FIGS. 2A and 2B.

The vehicle 10 also includes a plurality of sensing mechanisms, e.g., sensors or transducers 44, connected to the controller 40 and configured to monitor, track, and or detect various transmission parameters, as will be discussed in detail below. Correspondingly, the sensors 44 are configured to transmit signals S representative or indicative of the parameters monitored. By way of example, the transmission 14 is configured to deliver a detectable transmission output speed (N) to the output shaft 24, the transmission output speed (N) being directly or indirectly detectable, measurable, or otherwise determinable by a first sensing mechanism, e.g., one or more of the sensors 44, attached directly to or in proximity to output member 24. Similarly, a second, third and fourth sensing mechanism, e.g., one or more of sensors 44 of FIG. 1, connected to the controller 40, are preferably configured to monitor, track, or detect the running time, temperature, and shift or stop count of transmission 14, as will be described in further detail below. Those skilled in the art will recognize and understand that the means of communication between the sensors 41 and controller 40 is not restricted to the use of electric cables ("by wire"), but may be, for example, by radio frequency and other wireless technology, fiber-optic cabling, electromechanical communication, etc.

Alternatively, and particularly when transmission 14 is an automatic transmission, the sensors 44 may take the form of a control algorithm for transmission 14, i.e. programmed or stored in memory 42 of controller 40, and not embodied by a physical sensing device or mechanism. A "virtual" shift sensor (not shown) of this type may, for example, take the ratio of input speed (not shown) to output speed (N) of transmission 14, and compare the resultant ratio to known speed ratio values that are indicative of a completed shift event. The sensors 44, of whatever form, are preferably communicated with controller 40 via data link, such as Society of Automotive Engineers (SAE) Standards J1850 VWM and/or J1939, and/or via direct/hard wiring or other suitable communication link or connection.

The vehicle 10 also includes a service indicator device, depicted in FIG. 1 as service light 46, connected to the controller 40 in a manner similar to the sensors 44, described hereinabove. Alternatively, the service indicator device 46 might be a visual display or read-out (e.g. a liquid crystal display (LCD)), an acoustic warning (e.g. a beeping sound), a physical clue (e.g. a vibrating member), or any combination thereof.

Figure 2A:
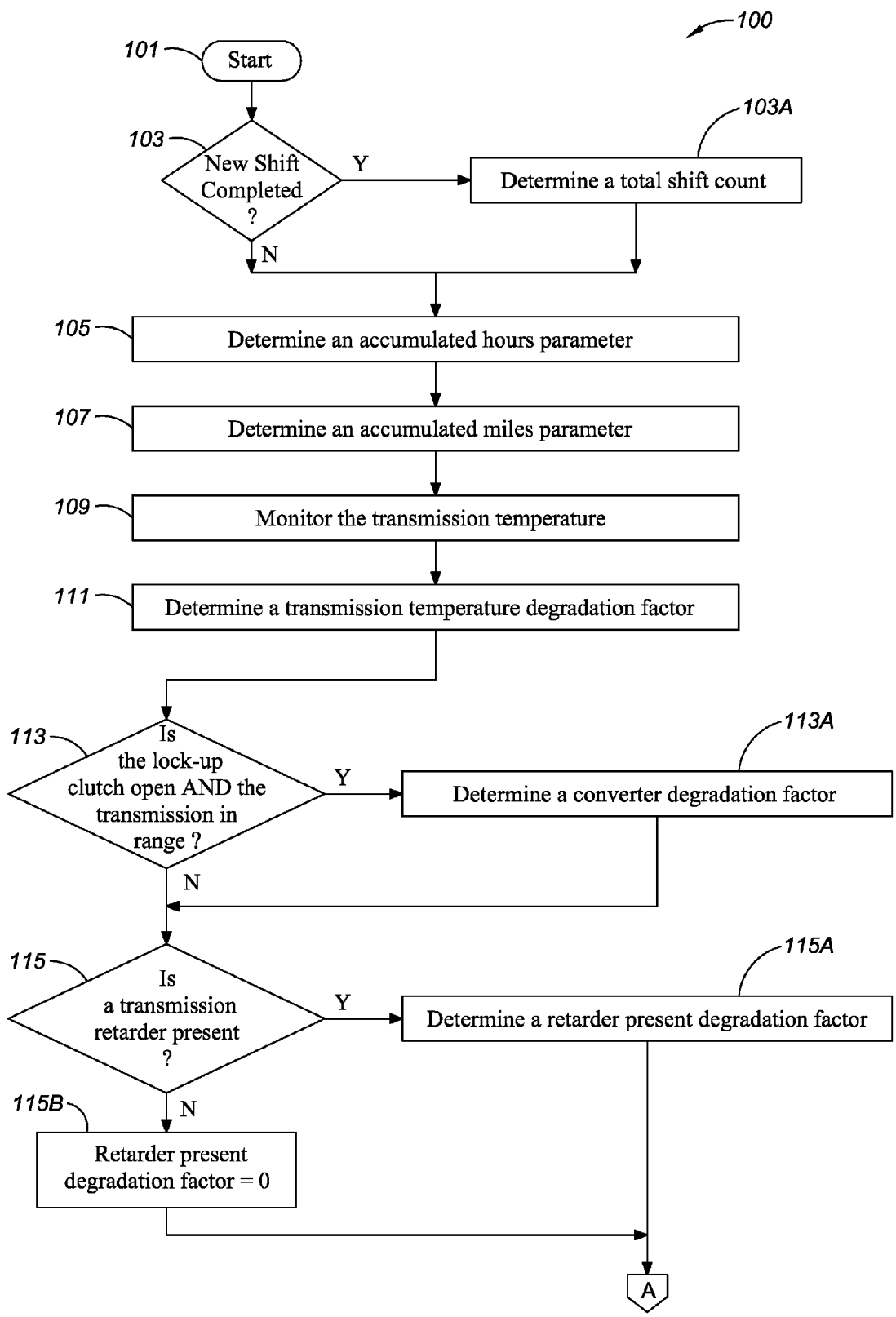
FIGS. 2A and 2B provide a flow chart illustrating the algorithm or method of determining or predicting the remaining useful life of transmission oil in accordance with the present invention.
Figure 2B:
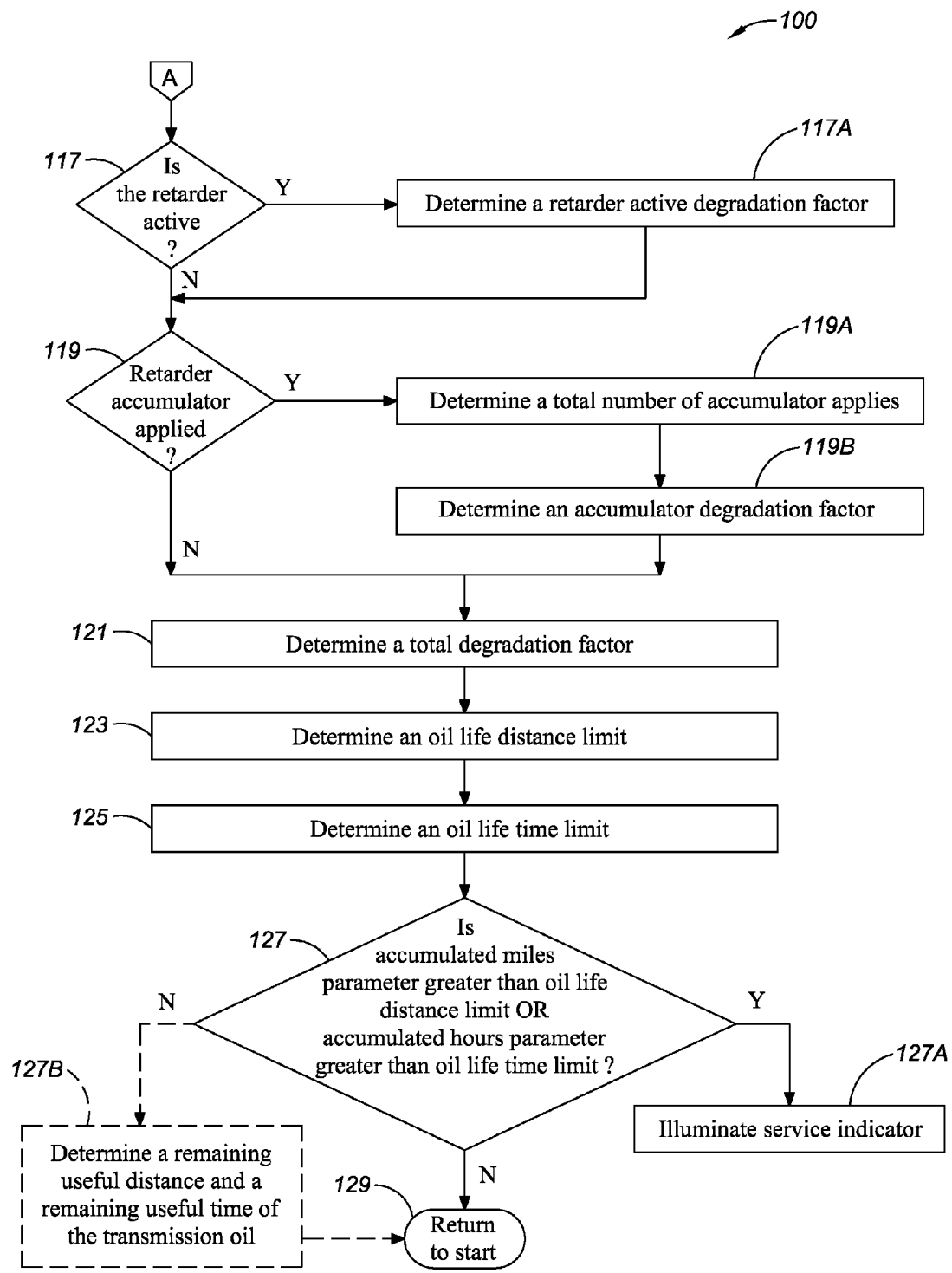

With reference now to the flow chart in FIGS. 2A and 2B of the drawings, the algorithm or method 100 of the present invention is shown for determining or predicting the remaining useful life of transmission oil. The method 100 continuously measures, tracks, or detects various transmission variables, such as, but not limited to, transmission temperature, percent of converter operation, retarder usage, retarder temperature, retarder installed, retarder accumulator applies, and shifts per mile, which may contribute to the aggregate degradation, or physical and chemical breakdown of transmission oil. The total degradation is used by the method or algorithm 100 to predict or determine the remaining useful life of the transmission oil—defined generally as the point at which the total accumulated hours of transmission oil use (AH) exceeds an oil life time (hours) limit (OIL_LH), and/or when the total accumulated distance (kilometers or miles) of transmission oil use (AM) exceeds an oil life distance (miles) limit (OIL_LM).

The method described herein may be employed in the respective embodiments described above; the methods being described with respect to the structure illustrated in FIG. 1. Although described herein with respect to transmission oil for a multi-speed power transmission of an automobile, the present invention may be applied in other various applications, such as, by way of example, aeronautical vehicles (e.g., airplanes, helicopters, etc.), agricultural vehicles (e.g., combine, tractor, etc.), construction vehicles (e.g., forklift, backhoe, excavator, etc.), and stationary machines (e.g., hydraulic press, hydraulic drill, etc.).

Looking to FIG. 2A, the method 100 begins at step 101. The base (or expected) useful life of transmission oil 21 is determined, preferably, by the number of shifts of transmission 14 per mile. In this regard, the method 100 includes, as step 103, monitoring or detecting when the transmission 14 has completed a new shift. If a new shift has been completed by the transmission 14, step 103A increments the total shift count (S_Count) to account for the new shift. S_Count=S_Count+1. If a new shift has not been completed, step 103A is omitted from the iteration. Alternatively or in addition thereto, step 103 can include tracking, monitoring or detecting when the vehicle 10 makes a stop and, in this particular instance, step 103A would then increment a total number of stops made by the vehicle 10 per mile.

Referring still to FIG. 2A, step 105 performs a calculation to adjust or determine the accumulated hours parameter (AH) of the transmission oil 21. The total accumulated hours parameter (AH) is determined based on when the engine 12 is running (e.g., according to a signal S from one of the plurality of sensors 44). To adjust the total accumulated hours parameter (AH), algorithm 100 performs a stored or programmed equation suitable for incrementing an "Accumulated Hours" value in memory 42. The preferred equation for calculating the total accumulated hours parameter (AH) is AH=AH+dt/3600, where (dt) equals a time increment measured in seconds.

Prior to, contemporaneous with, or after step 105, step 107 includes adjusting the accumulated miles parameter (AM)—algorithm 100 performs a stored or programmed equation suitable for incrementing an "Accumulated Miles" value in memory 42. The accumulated miles variable (AM) is preferably stored as miles when vehicle 10 is to be operated in the United States, but may be programmed in kilometers (km) or other distance measurements as required, depending on the intended use of the algorithm 100. The preferred equation performed in step 107 is "AM=AM+[N/3600][dt/(N/V)]", where the time increment (dt) is measured in seconds, and the ratio "N/V" equals the ratio of transmission output speed (N) in revolutions-per-minute to the actual vehicle speed (V), described previously hereinabove. The ratio (N/V) may be estimated, or may be predetermined based on the known axle ratio and/or diameter of a tire 32 of vehicle 10, and preprogrammed into memory 42. Optionally, controller 40 may be reprogrammed, for example, by an operator (not shown) of the vehicle 10 or by a service tool (not shown) to allow for extenuating circumstances, such as, but not limited to, aftermarket tires having a different diameter than originally specified.

Excessive degradation of the transmission oil may occur at high transmission temperatures. As such, the method 100 monitors, preferably in a continuous manner, the temperature of transmission 14 in step 109. In step 111, algorithm 100 accesses a set of "lookup tables" that are previously stored or programmed into memory 42 of controller 40 in order to retrieve data stored at a corresponding position in each of the tables. For example, the first lookup table is preferably a Transmission Temperature Severity Table, which provides a severity scalar, denoted hereinafter as (TTRANS_TL (TTRANS)), corresponding to various transmission temperatures. A transmission temperature "fuzzy timer" parameter (TTRANS_FT) will accumulate at different rates depending upon the current transmission temperature (TTRANS) and corresponding transmission temperature severity scalar (TTRANS_TL(TTRANS)). As is understood by those having ordinary skill in the art, a "fuzzy timer" or "fuzzy variable" is a timer/variable that does not necessarily increment in accordance with a prescribed set increment. The increment can vary depending on conditions set forth by an algorithm. Algorithm 100 selects or retrieves the corresponding transmission temperature severity scalar (TTRANS_TL(TTRANS)) value from the proper lookup table and, as step 111, calculates the transmission temperature fuzzy timer parameter (TTRANS_FT). TTRANS_FT=TTRANS_FT+TTRANS_TL(TTRANS)*dt/3600. From this value, the algorithm 100 calculates or determines, also as part of step 111, a transmission temperature degradation factor (TTRANS_DF). TTRANS_DF=1−AH/TTRANS_FT.

As is readily understood in the art, a calibrated factor is usually a scalar or offset that is applied to a software algorithm in an attempt to better make the algorithm simulate real world conditions without having to recompile the software to adjust parameters specific to the software. Making a parameter a "calibratable factor" allows for quick adjustments to be made, e.g., through a service tool, without affecting the actual code of the software.

The oil life of the transmission will be further degraded depending on the percentage of converter "non-lockup" operation. Correspondingly, at step 113 of FIG. 2A, the algorithm 100 monitors or detects whether a fluid coupling exists between engine 12 and transmission 14 via torque converter 16 (i.e., when the lockup clutch 18 is not applied, otherwise known as being in an "open state") and whether the transmission 14 is in range. The transmission 14 is said to be "in range" when the plurality of gear sets and clutch packs 17 are engaged by the controller 40 in order to achieve the necessary transmission of power between the engine 12 and the output shaft 24 and establish a reverse or forward speed ratio.

If the torque converter 16 is in operation and the transmission 14 is in range, a converter fuzzy timer parameter (CONV_FT) will accumulate, as part of step 113A, at different rates depending upon the current transmission temperature (TTRANS) and corresponding converter table lookup scalar (CONV_TL(TTRANS)). CONV_FT=CONV_FT+CONV_TL(TTRANS)*dt/3600. From this value, the algorithm 100 calculates or determines (also as part of step 113A) a converter degradation factor (CONV_DF), to be accounted for in the total degradation factor (TOTL_DF) to thereby decrease oil life expectancy for any corresponding converter operation. The converter degradation factor (CONV_DF) is calculated by dividing the converter fuzzy timer parameter (CONV_FT) by the total hours of operation on the oil (AH), and multiplying by a calibrated converter degradation factor (C_CONV_DF). CONV_DF=(CONV_FT/AH)*C_CONV_DF. If the torque converter 16 is not in operation (e.g., the lockup clutch 18 is active or in a "closed state"), or the transmission 14 is not in range, step 113A is omitted from the algorithm 100.

The method 100 also includes detecting whether the transmission 14 is built with a transmission retarder, such as retarder 26 of FIG. 1, as step 115. For example, the controller 40 can "autodetect" or monitor through a sensing mechanism, e.g. sensors 44 of FIG. 1, to see if a retarder 26 is installed, e.g., detect if certain retarder solenoids/circuits (not shown) are detected. Alternatively, the controller 40 can be calibrated during vehicle assembly to automatically recognize the presence of retarder 26. As seen in FIG. 2A, if the transmission 14 is built with a retarder 26, the oil life will be automatically decreased through a retarder present degradation factor (RTDR_P_DF), calculated in step 115A as being equal to a calibrated retarder degradation factor (C_RTDR_DF). RTDR_P_DF=C_RTDR_DF. If the transmission 14 is built without a retarder 26, the retarder present degradation factor (RTDR_P_DF) is set to zero in step 115B.

If a retarder 26 is present in the vehicle 10, retarder operation is tracked based on a miles-based "fuzzy" parameter. Looking to FIG. 2B of the drawings, step 117 detects, monitors, or tracks whether the retarder 26 is active. If the retarder 26 is active (i.e., step 117=Yes), algorithm 100 accesses another of the aforementioned "lookup tables" in order to retrieve a retarder table lookup scalar (RTDR_TL(TRTDR)), which is a severity factor quantifying various degrees of oil degradation attributable to corresponding variations in retarder temperature (TRTDR). A retarder fuzzy miles parameter (RTDR_FM) will accumulate, in step 117A, based on the output speed of the transmission (N) and the assumed output speed to vehicle speed ratio (N/V). This parameter is then multiplied by retarder table lookup scalar (RTDR_TL (TRTDR)) to adjust the rate at which the retarder fuzzy miles parameter (RTDR_FM) will accumulate. RTDR_FM=RTDR_FM+RTDR_TL(TRTDR)*N/3600*dt/(N/V).

Also as part of step 117A, FIG. 2B, a retarder active degradation factor (RTDR_A DF) is calculated or determined, to be accounted for in the total degradation factor (TOTL_DF) to thereby decrease the transmission oil life for any corresponding retarder operation. In this regard, the retarder active degradation factor (RTDR_A DF) is calculated by algorithm 100 by dividing the modified retarder miles parameter (RTDR_FM) by the total accumulated miles (AM), and multiplied by a calibrated retarder degradation factor C_RTDR_DF. RTDR_A_DF=(RTDR_FM/AM)*C_RTDR_DF. If the retarder 26 is not active, step 117A is omitted from the algorithm 100.

Still referring to FIG. 2B, the algorithm 100 also includes tracking or monitoring the number of applications of the fluid accumulator 25. When the retarder 26 is required to make a quick apply, the accumulator 25 is activated to stroke (or apply) a volume of fluid 21 to the retarder 26, which can further degrade the transmission oil 21, thereby reducing oil life. As such, step 119 includes detecting if the accumulator 25 is applied and, in response to the accumulator 25 being applied, incrementing a total number of accumulator applies (ACML_A) in step 119A.

In step 119B, an accumulator degradation factor (ACML_DF) is calculated or determined, to be accounted for in the total degradation factor (TOTL_DF) to thereby decrease oil life for any corresponding accumulator operation. Correspondingly, the accumulator degradation factor (ACML_DF) is calculated by multiplying the total number of accumulator applies (ACML_A) by a calibrated accumulator degradation factor (C_ACML_DF) for every 100,000 accumulator applies. ACML_DF=(ACML_A/100,000)*C_ACML_DF. Notably, if the transmission 14 is built without a retarder 26, as detected in step 115, steps 117 and 119, and any corresponding steps, can be omitted from the algorithm 100.

In steps 123 and 125, the final oil life limits—namely, the oil life time (hours) limit (OIL_LM) and oil life distance (miles) limit (OIL_LH), are determined. Prior to, or contemporaneously with steps 123 and 125, the total degradation factor (TOTL_DF) is calculated in step 121, for example, by taking the sum of all of the transmission oil degradation factors, including, but not limited to, the transmission temperature degradation factor (TTRANS_DF), the converter degradation factor (CONV_DF), the retarder present degradation factor (RTDR_P_DF), the retarder active degradation factor (RTDR_P_DF), and the accumulator degradation factor (ACML_DF). After each shift is counted and the total shift count (S_Count) determined (steps 103 and 103A), step 123 includes dividing the total shift count (S_Count) by the total number of accumulated miles (AM). The shift count (S_Count) (or, alternatively, the stops per mile count) is used by the controller 40 to look up an oil life distance scalar (TL(S_COUNT/AM)) and an oil life time scalar (TL(S_COUNT/AH)) in one of the various aforementioned lookup tables. Finally, step 123 and 125 respectively include calculating the oil life distance (miles) limit (OIL_LM) and oil life time (hours) limit (OIL_LH) by taking the respective result from the table lookup (TL(S_COUNT/AM)), (TL(S_COUNT/AH)), and multiplying by the total degradation factor (TOTL_DF). OIL_LM=TL(S_COUNT/AM)*TOTL_DF and OIL_LH=TL(S_COUNT/AH)*TOTL_DF.

In step 127, the controller 40 determines or monitors whether the total accumulated hours (AH) of transmission oil use exceeds the oil life time limit (OIL_LH), and/or whether the total accumulated miles (AM) of transmission oil use exceeds the oil life distance limit (OIL_LM). If either the accumulated hours (AH) is greater than the oil life time limit (OIL_LH) or the accumulated miles (AM) is greater than the oil life distance limit (OIL_LM), the method 100 responds in step 127A by activating the service indicator device 46 to notify the vehicle operator or maintenance personnel (not shown) that oil service is required. If the accumulated hours (AH) is not greater than the oil life hours limit (OIL_LH) and the accumulated miles (AM) is not greater than the oil life miles limit (OIL_LM), step 129 directs that the algorithm 100 stop and return to step 101.

In addition, or as an alternative, the method 100 also includes, as part of step 127 or as a separate step 127B, determining the remaining useful distance (UD) of the transmission oil 21 in response to the accumulated miles (AM) variable and a remaining useful time (UT) of the transmission oil 21 in response to the accumulated hours (AH) variable. In this instance, it is also preferred that the service indicator device 46 be configured (e.g., as a liquid crystal display (LCD) or service tool for viewing a J1939 parameter) to selectively provide the remaining useful distance (UD) and the remaining useful time (UT) to the occupants of the vehicle. Preferably, the service indicator device 46 may be cleared or disabled by the driver or by the maintenance personnel via a service tool.

The method 100 of the present invention preferably includes at least steps 101-127. However, it is within the scope and spirit of the present invention to omit steps, include additional steps, and/or modify the order presented in FIGS. 2A and 2B. It should be further noted that the method 100 depicted in FIGS. 2A and 2B represents a single cycle in predicting the remaining useful life of automatic transmission oil. As such, it is contemplated, but not required, that the method 100 be applied in a systematic and continuous manner throughout the operational life of a transmission.

While the best modes for carrying out the invention have been described in detail, those familiar with the art to which this invention relates will recognize various alternative designs and embodiments for practicing the invention within the scope of the appended claims.

The invention claimed is:

1. A method for determining the remaining useful life of oil in a transmission having a torque converter with a lockup clutch, the method comprising:
   detecting if the transmission has completed a new shift;
   determining a total shift count if said new shift has been completed;
   determining an accumulated time parameter;
   determining an accumulated distance parameter;
   determining a transmission temperature degradation factor based at least in part upon the accumulated time parameter;
   determining a total degradation factor based at least in part upon said transmission temperature degradation factor;
   determining an oil life time limit based at least in part upon said total degradation factor; the total shift count, and the accumulated time parameter
   determining if said accumulated time parameter is greater than said oil life time limit;
   determining an oil life distance limit based at least in part upon said total degradation factor; the total shift count, and the accumulated distance parameter
   determining if said accumulated distance parameter is greater than said oil life distance limit; and
   activating a service indicator configured to signal that transmission oil service is required in response to at least one of said accumulated time parameter being greater than said oil life time limit and said accumulated distance parameter being greater than said oil life distance limit.

2. The method of claim 1, wherein said determining a transmission temperature degradation factor is based at least in part upon a transmission temperature fuzzy timer parameter.

3. The method of claim 1, further comprising:
   detecting if the lockup clutch is open and the transmission is in range; and
   determining a converter degradation factor if the lockup clutch is open and the transmission is in range;
   wherein said determining a total degradation factor is further based at least in part upon said converter degradation factor.

4. The method of claim 3, wherein said determining a converter degradation factor is based at least in part upon a converter fuzzy timer parameter.

5. The method of claim 1, further comprising:
   detecting if a transmission retarder is present; and
   determining a retarder present degradation factor if said transmission retarder is present;
   wherein said determining a total degradation factor is further based at least in part upon said retarder present degradation factor.

6. The method of claim 5, further comprising:
   detecting if said transmission retarder is active; and determining a retarder active degradation factor if said transmission retarder is active;
wherein said determining a total degradation factor is further based at least in part upon said retarder active degradation factor.

7. The method of claim 6, wherein said determining a retarder active degradation factor is based at least in part upon a retarder fuzzy miles parameter.

8. The method of claim 5, further comprising:
detecting if a retarder accumulator is applied; and
determining an accumulator degradation factor if said accumulator is applied;
wherein said determining a total degradation factor is further based at least in part upon said accumulator degradation factor.

9. The method of claim 1, further comprising:
determining at least one of a remaining useful distance of the transmission oil based at least in part upon said accumulated distance parameter and a remaining useful time of the transmission oil based at least in part upon said accumulated time parameter.

10. The method of claim 9, wherein said service indicator is further configured to selectively communicate at least one of said remaining useful distance and said remaining useful time of the transmission oil to vehicle occupants.

11. A method for determining the remaining useful life of transmission oil in a motorized vehicle including a power transmission having a torque converter with a lockup clutch, the method including:
detecting if the transmission has completed a new shift;
determining a total shift count when said new shift has been completed;
determining an accumulated distance parameter;
determining an accumulated time parameter;
monitoring a transmission temperature;
determining a transmission temperature degradation factor based at least in part upon the transmission temperature, and the accumulated time parameter;
detecting if the lockup clutch is open and if the transmission is in range;
determining a converter degradation factor if the lockup clutch is open and the transmission is in range;
determining a total degradation factor based at least in part upon said transmission temperature degradation factor and said converter degradation factor;
determining an oil life time limit and an oil life distance limit each based at least in part upon said total degradation factor and said total shift count;
determining if at least one of said accumulated time parameter is greater than said oil life time limit and said accumulated distance parameter is greater than said oil life distance limit; and
activating a service indicator configured to notify vehicle occupants that transmission oil service is required in response to at least one of said accumulated time parameter being greater than said oil life time limit and said accumulated distance parameter being greater than said oil life distance limit.

12. The method of claim 11, wherein said determining a transmission temperature degradation factor is based at least in part upon a transmission temperature fuzzy timer parameter, and said determining a converter degradation factor is based at least in part upon a converter fuzzy timer parameter.

13. The method of claim 11, further comprising:
detecting if a transmission retarder is present; and
determining a retarder present degradation factor if said transmission retarder is present;
wherein said determining a total degradation factor is further based at least in part upon said retarder present degradation factor.

14. The method of claim 13, further comprising:
detecting if said transmission retarder is active; and
determining a retarder active degradation factor based at least in part upon a retarder fuzzy miles parameter if said transmission retarder is active;
wherein said determining a total degradation factor is further based at least in part upon said retarder active degradation factor.

15. The method of claim 13, further comprising:
detecting if a retarder accumulator is applied;
determining a total number of accumulator applies; and
determining an accumulator degradation factor based at least in part upon said total number of accumulator applies;
wherein said determining a total degradation factor is further based at least in part upon said accumulator degradation factor.

16. The method of claim 11, further comprising:
determining at least one of a remaining useful distance of the transmission oil based at least in part upon said accumulated distance parameter and a remaining useful time of the transmission oil based at least in part upon said accumulated time parameter;
wherein said service indicator is further configured to selectively communicate at least one of said remaining useful distance and said remaining useful time of the transmission oil to vehicle occupants.

17. A control apparatus for a motorized vehicle with a transmission having a torque converter with a lockup clutch and a reservoir fluidly coupled to and configured for supplying transmission oil to the power transmission, the control apparatus comprising:
a controller in operative communication with the power transmission;
at least one sensing device operatively connected to said controller and configured to monitor a plurality of transmission degradation factors; and
a service indicator operatively connected to said controller and configured to signal that transmission oil service is required;
wherein said controller is programmed and configured to determine an accumulated time parameter and accumulated distance parameter, detect if the transmission has completed a new shift, and determine a total shift count if said new shift has been completed;
wherein said plurality of transmission degradation factors are based at least in part upon at least one of the accumulated time parameter, and the accumulated distance parameter;
wherein said controller is programmed and configured to determine a total degradation factor based at least in part upon said plurality of transmission degradation factors;
wherein said controller is programmed and configured to determine an oil life time limit and an oil life distance limit based at least in part upon said total degradation factor and said total shift count;
wherein said controller is programmed and configured to determine if at least one of said accumulated time parameter is greater than said oil life time limit and said accumulated distance parameter is greater than said oil life distance limit; and
wherein said controller activates said service indicator in response to at least one of said accumulated time parameter being greater than said oil life time limit and said accumulated distance parameter being greater than said oil life distance limit.

18. The control apparatus of claim 17, wherein said plurality of transmission degradation factors includes a transmission temperature degradation factor, a converter degradation factor, a retarder present degradation factor, a retarder active degradation factor, and an accumulator degradation factor.

19. The control apparatus of claim 17, wherein said controller is further programmed and configured for determining at least one of a remaining useful distance of said transmission oil in response to said accumulated distance parameter and a remaining useful time of said transmission oil in response to said accumulated time parameter;

wherein said service indicator device is configured to selectively display said remaining useful distance and said remaining useful time to vehicle occupants.

* * * * *